(12) United States Patent
Murrell

(10) Patent No.: US 6,190,704 B1
(45) Date of Patent: Feb. 20, 2001

(54) REGULATION OF WOUND HEALING BY NITRIC OXIDE

(75) Inventor: George Anthony Calvert Murrell, New York, NY (US)

(73) Assignee: New York Society for the Ruptured and Crippled Maintaining the Hospital for Special Surgery, New York, NY (US)

( * ) Notice: Under 35 U.S.C. 154(b), the term of this patent shall be extended for 0 days.

(21) Appl. No.: 08/311,545

(22) Filed: Sep. 23, 1994

(51) Int. Cl.$^7$ .......................... A61K 33/00; A61K 45/00
(52) U.S. Cl. .............................. 424/718; 514/1; 514/611; 514/789
(58) Field of Search .............................. 514/310, 1, 611, 514/789; 424/718

(56) References Cited

U.S. PATENT DOCUMENTS

| | | | |
|---|---|---|---|
| 4,883,661 | * 11/1989 | Daly et al. | 424/85.1 |
| 5,053,387 | * 10/1991 | Alexander | 514/2 |
| 5,145,681 | * 9/1992 | Fortney et al. | 424/94.63 |
| 5,221,668 | * 6/1993 | Henningfield et al. | 514/23 |
| 5,405,919 | * 4/1995 | Keefer et al. | 525/377 |
| 5,428,135 | * 6/1995 | Lyons et al. | 530/399 |
| 5,504,117 | * 4/1996 | Gorfine | 514/749 |
| 5,519,020 | * 5/1996 | Smith et al. | 424/718 |
| 5,576,287 | * 11/1996 | Zaloga et al. | 514/2 |
| 5,789,447 | * 8/1998 | Wink, Jr. et al. | 514/611 |
| 5,814,666 | * 9/1998 | Green et al. | 514/611 |

OTHER PUBLICATIONS

Jensen et al., Medline AN 83094628 (Sep. 1982).*
Pechinot et al., Medline AN 91351722 (May 1991).*
Plotnikova et al., Medline AN 92271625 (1992).*
Baird et al., Medline AN 90372611 (Sep. 1990).*
Smith et al., Wounds, 3 (1), pp.50–58 (1991).*
Moncada et al., "The L–Arginina–Nitric Oxide Pathway", The New England Journal of Medicine, pp2002–2012.*
Konturek et al., "Inhibition of Nitric Oxide Synthese delays healing of Chronic gastric vlears", European Journal of Pharmacology, 239,pp.215–217.*
Tarry et al. "L–Arginina Improves Endothalium–Dependent Vasorelaxation and Reduces Intimal Hyperplasia AfterBukoon Angioplasty", Arteriosclerosis and Thrombosis 1466) , Jun. 1994, pp.938–943.*
Baum "Complexes Control Nitric Oxide Release", C & En Sep. 1992, pp. 32–33.*
Bult, H. et al., Nitric Oxide as an Inhibitory Non–Adrenergic Non–Cholinergic Neutrotransmitter, Nature, 345:346–347 May 1990.
Dawson, T.M. et al., Nitric Oxide Synthase and Neuronal NADPH Diaphorase are Identical inn Brain and Peripheral Tissue, Proc. Natl. Acad. Sci. USA, 88:7797–7801, Sep. 1991.

Drago, R.S., Free Radicals in Oragnic Chemistry (Advanced in Chemistry Series), Number36,pp. 143–149, Sep. 1962.
Giovanelli, J. et al., Tetrahydrobiopterin, A Cofactor for Rat Cerebellar Nitric Oxides Synthase, Does not Function as a Reactant in the Oxegenation of Arginine, Proc. Nat. Acad. Sci. USA, 88:7091–7095, Aug. 1991.
Green et al. Analysis of Nitrate, Nitrite, and [$^{15}$n]Nitrate inn Biological Fluids , Anal. Biochem., 126:131, Oct.1982.
Heck et al., Epidermal Growth Factor Suppresses Nitric Oxide and Hydrogen Peroide Production by Keratinocytes, J. Biol. Chem., 267:21277, Oct.1992.
Hevel, J.M. et al., Purification of the Inducible Murine Microphage Nitric Oxide Synthase, J. Biol. Chem., 266:22789–22791, Dec. 1991.
Hibbs, J.B. et al, Nitric Oxide: A Cytotoxic Activated Macrophage Effector Molecule, Biochem. Biophys. Res. Comm., 157:87–94, Nov. 1988.
Hrabie et al., New Nitric Oxide–Releasing Zwitterions Derived from Polyamines, J. Org. Chem., 58:1472, Mar. 1993.
Knowles, R.G. et al., Formation of Nitric Oxide from L–arginine in the Central Nervous System: A transduction Mechanism for Stimulation of the Soluble Guanylate Cyclase, Proc. Natl. Acad. Sci. USA, 86:5159–5162, Jul. 1989.
Maragos et al., Complexes of NO with Nucleophiles as Agents for the Controlled Biological Release of Nitric Oxide. Vasorelaxant Effects J. Med. Chem., 34:3242, Nov. 1991.
Mollace, V. et al., Cultured Astrocytoma Cells Inhibit Platelet Aggregation by Relleasing a Nitric Oxide–Like Factor, Biochem. Biophys. Res. Comm., 172:564–9, Oct. 1990.
Moncada, S. et al., The L–arginine–Nitric Oxide Pathway, New Engl. J. Med., 329 (27):2002–12, Dec. 1993.
Moroz, L.L. et al., Nitric Oxide Activates Buccal Motor Patterns in Lymnaea Stagnalis, Neuroreport, 4:643–6, Jun. 1993.
Mulligan et al., Tissue Injury Caused by Deposition of Immune Complexes is L–arginine Dependent, Proc. Natl. Acad. Sci. USA, 88:6338, Jul. 1991.
Nathan, C.F. et al., Role of Nitric Oxide Synthesis in Macrophage Antimicrobial Activity, Curr. Opin. Immunol., 3:65–7, 1991.
Palmer, R.M. et al., Induction of Nitric Oxide Synthase In Human Chondrocytes, Biochem. Biophys. Res. Comm., 193:398–405, May 1993.

(List continued on next page.)

Primary Examiner—Jeffrey C. Mullis
(74) Attorney, Agent, or Firm—Darby & Darby

(57) ABSTRACT

The present invention provides methods and compositions for promoting healing of damaged tissue that result in an increased level of nitric oxide in the vicinity of the damaged tissues. Also provided are methods and compositions for inhibiting unwanted wound healing by inhibiting the activity of nitric oxide in the tissue.

7 Claims, 10 Drawing Sheets

OTHER PUBLICATIONS

Palmer, R.M.J. et al., Nitric Oxide Release Accounts for the Biological Activity of Endothelium–Derived Relaxing Factor, Nature, 327:524–527, Jun. 1987.

Palmer, R.M.J. et al., Vascualar Endothelial Cells Synthesize Nitric Oxide from L–arginine, Nature 333:664–6, Jun. 1988.

Rand, M.J. et al., Nitrergic Transmission: Nitric Oxide as a Mediator of Non–Adrenergic, Non–Cholingeric Neuro–Effector Transmission, Clin. Exp. Phamacol. Physiol., 19:147–69, 1992.

Salvemini, D. et al., Synthesis of a Nitric Oxide–Like Factor from L–aginine by Rat Serosal Mast Cells: Stimulation of Guanylate Cyclase and Inhibition of Platelet Aggregation, Biochem. Biophys. Res. Comm., 169:596–601, Jun. 1990.

Snyder, S.H., Janus Faces of Nitric Oxide, Nature, 364:577–632, Aug. 1993.

Stadler, J. et al., Articular Chondrocytes Synthesize Nitric Oxide inn Response to Cytokines and Lipopolysaccharide, J. Immunol., 147:3915–20, Dec. 1991.

Szabo, C. et al., Platelet–Activating Factor Contributes to the Induction of Nitric Oxide Synthase by Bacterial Lipopolysaccharide, Circulation Res., 73:73, Dec. 1993.

Ward, S.M. et al., NADPH Diaphorase and Nitric Oxide Synthase Colocalization in Enteric Neurons of Canine Proximal Colon, Am. J. Physiol, 263G277–84, 1992.

Bulgrin, J.P. et al., Arginine–Free Diet Suppresses Nitric Oxide Production in Wounds, J. Nutr. Blochem., 4:588–593, 1993.

* cited by examiner

REGULATION OF WOUND HEALING BY NITRIC OXIDE

FIELD OF THE INVENTION

This invention pertains to methods for regulating the healing of damaged tissue by adjusting the concentration of nitric oxide in the vicinity of the damaged tissue.

BACKGROUND OF THE INVENTION

Nitric oxide (NO•) is synthesized from the amino acid L-arginine by a family of enzymes termed nitric oxide synthases. Its small size and its unpaired electron (denoted•), make it a highly reactive and locally diffusible free radical. Since the discovery in 1987 that endothelium derived relaxing factor (EDRF) is, in fact, NO•, (Palmer, R. M. J. et al., 1988, Nature 333:664–6; Palmer, R. M. J. et al., 1987, Nature, 327:524–527) it has become evident that NO• is a widely distributed and multi-functional intra- and intercellular messenger. There is strong evidence that NO• synthesized by vascular endothelium is responsible for the regulation of blood pressure and the control of platelet aggregation (Mollace, V. et al., 1990, Biochem. Biophy. Res. Comm., 172:564–9; Rand, M. J. et al., 1992, Clin. Exp. Phamacol. Physiol., 19:147–69; Szabo, C. et al., 1993, Circulation Res., 73:73), and may be involved in vascular injury caused by tissue deposition of immune complexes (Mulligan et al., Proc. Natl. Acad. Sci. USA, 88:6338, 1991). In the central nervous system, nitric oxide is thought to be a neurotransmitter involved in memory and motor function (Bult, H. et al., 1990, Nature, 345:346–347; Dawson, T. M. et al., 1991, Proc. Natl. Acad. Sci. USA, 88:7797–7801; Giovanelli, J. et al., 1991, Proc. Natl. Acad. Sci. USA, 88:7091–7095; Moroz, L. L. et al., 1993, Neuroreport, 4:643–6; Knowles, R. G. et al., 1989, Proc. Natl. Acad. Sci. USA, 86:5159–5162; Snyder, S. H., 1993, Nature, 364:577–632). In the peripheral nervous system, a widespread network of nonadrenergic, noncholinergic nerves use nitric oxide to modulate gastrointestinal, bladder and (corpus cavernosum relaxation and erection. (Moncada, S. et al., 1993, New Engl. J. Med., 329 (27):2002–12; Ward, S. M. et al., 1992, Am. J. Physiol, 263:G277–84).

NO• is produced in large amounts by an inducible isoform of nitric oxide synthase in macrophages, neutrophils, lymphocytes and peripheral-blood monocytes during immunological reactions and septic shock. (Hevel, J. M. et al., 1991, J. Biol. Chem., 266:22789–22791; Hibbs, J. B. et al, 1988, Biochem. Biophys. Res. Comm., 157:87–94; Nathan, C. F. et al., 1991, Curr. Opin. Immunol., 3:65–70; Salvemini, D. et al., 1990, Biochem. Biophys. Res. Comm., 169:596–601; Szabo, C. et al., 1993, Circulation Res., 73:73). NO• is also produced in keratinocytes in response to inflammatory mediators (Reck et al., J. Biol. Chem., 267:21277, 1992.) There is also an inducible form of nitric oxide synthase in cartilage. (Murrell, G. A. C. et al., 1994, International, Business Communications 3rd Symposium on Nitric Oxide: Palmer, R. M. et al., 1993, Biochem. Biophys. Res. Comm., 193:398–405; Stadler, J. et al., 1991, J. Immunol, 147:3915–20) Constitutive, $Ca^{++}$ dependent isoforms of the enzyme found in the brain and blood vessels release NO• at low, relatively stable concentrations.

The present invention relates to a previously uncharacterized role for NO in wound healing. Wound healing involves the recruitment of inflammatory cells, followed by fibroblasts, to the site of the wound, where collagen and other connective tissue elements are deposited. The collagen fibers then gradually realign to resemble the original connective tissue (e.g. tendon, ligament, skin.) The ability to regulate this process locally and specifically would be of considerable therapeutic importance e.g. after surgery or trauma. Furthermore, in certain pathological situations, such as arthrofibrosis, Dupuytren's contracture, peritoneal adhesions, frozen shoulder, scleroderma, and keloid formation, over-expression, and sometimes normal expression, of the repair mechanisms has negative consequences, and it would be desirable to selectively suppress this response.

Conversely, there are many situations in which the healing response in wound healing is delayed or inhibited e.g. in patients with systemic diseases such as liver failure, renal impairment, diabetes, peripheral vascular disease, or in patients taking drugs that inhibit healing e.g. corticosteroids or immunosuppressive agents. In these cases, additional exogenous NO• may enhance the healing response.

Therefore, there is a need in the art for methods and compositions to influence wound healing in a temporally and spatially regulatable manner.

SUMMARY OF THE INVENTION

It has now unexpectedly been found that NO• acts as an early initiator of wound healing in mammals. The present invention encompasses a method for promoting the healing of a damaged tendon or other soft tissue in a patient in need of such treatment, by exposing the tissue or tendon to an increased concentration of NO•. This increased concentration or level of NO• may be achieved by contacting the damaged soft tissue or tendon with an agent that increases the local concentration of NO• i.e. the concentration of NO• within, or in the immediate vicinity of, the damaged tendon. The agent may be a compound that increases the activity of NO synthase (NOS) within the tendon, or a compound that provides NO• as a breakdown product.

In another aspect, the invention encompasses a method for inhibiting unwanted wound healing in a patient in need of such treatment, as in e.g. arthrofibrosis, Dupuytren's contracture, peritoneal adhesions, frozen shoulder, scleroderma, or keloid formation, by contacting the affected tissue with an agent that inhibits the activity of nitric oxide synthase in the tissue.

In another aspect, the invention provides pharmaceutical compositions; for promoting the healing of a damaged tissue, comprising an agent that increases the concentration or level of nitric oxide in the vicinity of the damaged tissue. The invention also provides pharmaceutical compositions for inhibiting unwanted wound healing in or near a damaged tissue, comprising an agent that reduces the concentration or level of nitric oxide in the vicinity of the damaged tissue.

In still another aspect, the invention provides a method for identifying agents that stimulate the production of nitric oxide in damaged tendons, which comprises the steps of:
  (i) administering a test compound to a mammal;
  (ii) damaging the Achilles tendon in the mammal;
  (iii) allowing the damaged tendon to heal for a predetermined time;
  (iv) measuring nitric oxide synthase activity in the tendon; and
  (v) comparing the nitric oxide synthase activity with the nitric oxide synthase activity in an untreated, damaged tendon to determine that the compound causes a significant increase in nitric oxide synthase activity over that observed in a control tendon.

In still another aspect, the invention provides a method for identifying agents that inhibit unwanted wound healing, which comprises the steps of:

(i) administering a test compound to a mammal;

(ii) damaging the Achilles tendon in the mammal;

(iii) allowing the damaged tendon to heal for a predetermined time;

(iv) measuring the activity of nitric oxide synthase in the tendon; and (v) comparing the nitric oxide synthase activity with the nitric oxide synthase activity in an untreated damaged tendon to determine that the compound causes a significant decrease in nitric oxide synthase activity over that observed in a control tendon.

DETAILED DESCRIPTION OF THE INVENTION

All patent applications, patents, and literature references cited in this specification are hereby incorporated by reference in their entirety. In case of inconsistencies, the present description, including definitions, will control.

The present invention is directed to enhancing or retarding the natural biological healing process of damaged tendons, ligaments, bones, skin, cornea, and other tissues by regulating the levels of nitric oxide (NO•) in a spatially and temporally defined manner.

It has been found that local increases in NO• concentrations initiate and enhance wound healing. As shown in Example 1 below, an experimentally induced lesion in the Achilles tendon of a rat causes a transient increase in the activity of nitric oxide synthase (NOS) in the tendon. Furthermore, inhibition of NOS using Nw-nitro-L-arginine methyl ester (L-NAME) depresses the healing process. On this basis, it is contemplated that agents that induce NOS activity and thus increase the local NO• concentration, as well as agents that provide a direct source of NO• (NONOates), will be useful in promoting wound healing. Alternatively, in pathological conditions where repair mechanisms are deleterious, agents that inhibit NOS or, alternatively, agents that scavenge NO•, should be useful in selectively suppressing these processes.

In order to be effective in enhancing wound healing, the concentration or level of NO• to which the wounded tissue is exposed should be increased by at least about 150% and up to about 10,000% (i.e. 100-fold). Preferably, the amounts of NO• to which the wounded tissue is exposed as a result of the treatment is between about 150% and about 1000% higher as compared with the amount of NO• to which the wounded tissue is exposed in the absence of such treatment. The most preferred range is between about 400% and about 1000% the amount of NO• to which the wounded tissue is normally exposed.

Conversely, in order to be effective in inhibiting wound healiing, the concentration or level of NO• to which the tissue is exposed should be decreased by at least 50% and up to 100% of the amount of NO• to which the tissue is exposed in the absence of treatment. Preferably, NO• is decreased by at least 75%, and most preferably, by at least 90%.

Figure 1:
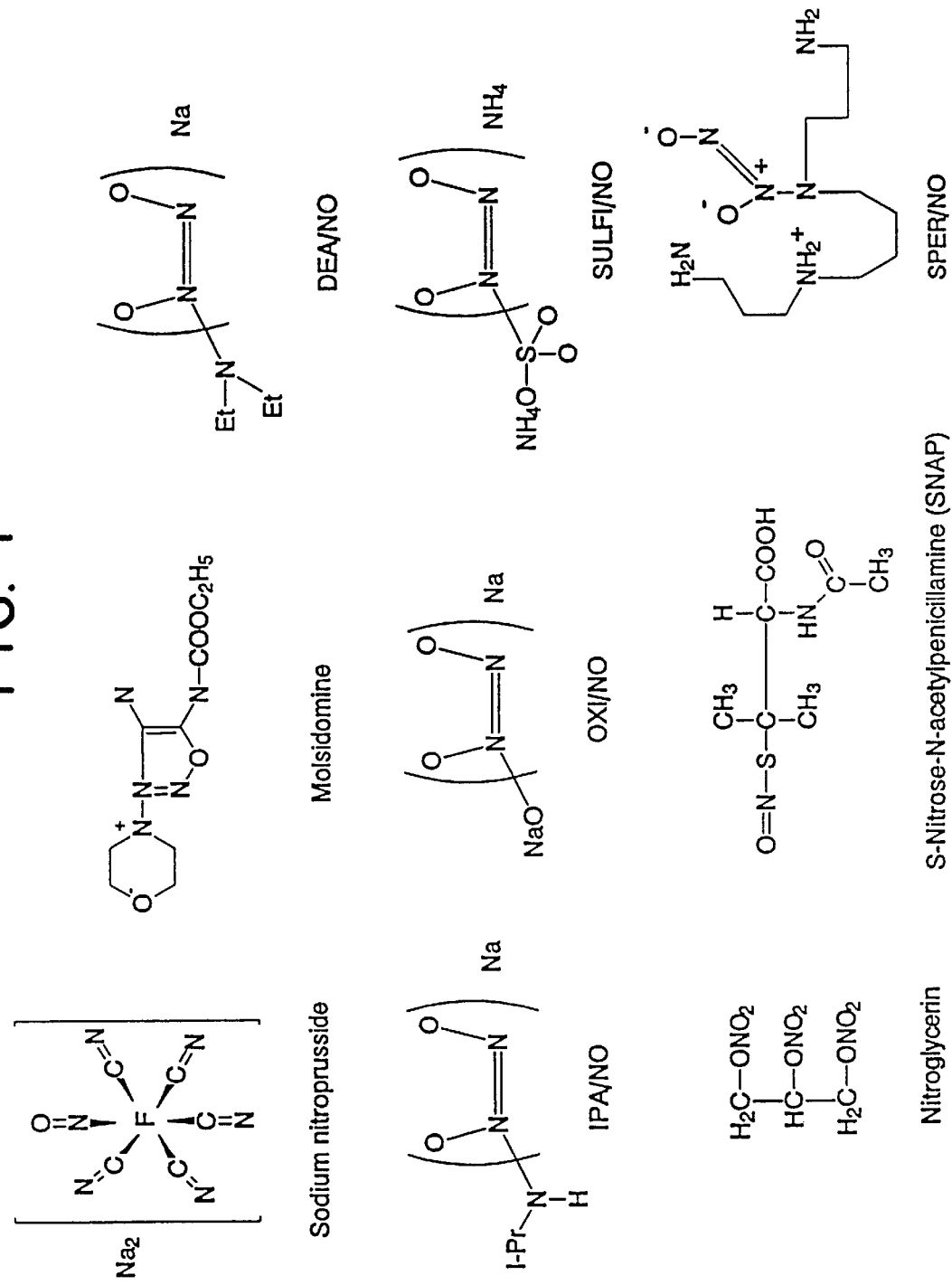
FIG. 1 shows the structures of several NONOates i.e. agents that release NO•.

The present invention encompasses the therapeutic use of agents that stimulate or inhibit NO• production in clinical practice. The compounds that may be employed to enhance NO• in the vicinity of damaged tissue include without limitation sodium nitroprusside; N-(Ethoxycarbonyl)-3-(4-morpholinyl)sydnone imine (Molsidomire); 3-morpholinosydnonimine (SIN-1); 1,2,3,4-Oxatriazolium, 5-amino-3-(3,4-di-chlorophneyl)-chloride (GEA 3162); 1,2, 3,4-Oxatriazolium, 5-amino-3-(30chloro-2-methyl-phenyl) chloride(GEA5024); 1,2,3,4-Oxatriazolium,3-(3-chloro-2-methylphenyl)-5-[[[cyanomethylamino]carbonyl]amino]-hydroxide inner salt (GEA5583);S-nitroso-N-acetyl-D,L-penicillamine(SNAP);1-[(4', 5'-Bis(carboxymethoxy)-2'-nitrophenyl)methoxy]-2-oxo-3,3,diethyl-1-triazene dipotassium salt (CNO-4); and [1-(4', 5'-Bis (carboymethoxy)-2'-nitrophenyl)methoxy]-2-oxo-3, 3-diethyl-1-triazine diacetoxymethyl ester (CNO-5), all of which are available from Alexis Corp. (San Diego, Calif.). Additional compouZnds include nitroglycerin, diethylamine-NO (DEA/NO), IPA/NO, sperinine-NO (SPER/NO), sulfite-NO (SULFI/NO), OXI/NO, and DETA/NO, the synthesis of which is described in Drago, R. S., in *Free Radicals in Organic Chemistry* (Advances in Chemistry Series), Number 36, pages 143–149, 1962; and in Maragos et al., *J. Med. Chem.* 34:3242, 1991. Briefly, these compounds are prepared by reaction of nitric oxide with a nucleophile. The preferred NO•-generating compound is DETA/NO-(diethylenetriamine/NO), which has a half-life of about 1 day and is thus particularly suited for sustained-released formulations described below (Hrabie et al., *J. Org. Chem.* 58:1472, 1993). The structures of some of these compounds, which are collectively known as NONOates, are illustrated in FIG. 1.

The compounds that may be employed to reduce the concentration of NO• in the vicinity of damaged tissue include without limitation L-NAME, monomethyl arginine (NMMA), aminoguanidine or its derivatives, and N-w-nitro-L-arginine (L-NMA). The preferred compound to use to reduce NO• in the vicinity of damaged tissue is NMMA (Alexis Corp., San Diego, Calif.). In addition, compounds such as CPTIO (2-(4-carboxypheniyl)-4,4,5,5-tetramethylimidazoline-1-oxyl-3-oxide Alexis Corp.) that scavenge NO• may also be used.

In addition to the compounds identified above, it is possible to use other NO•-generating or NO•-inhibiting compounds, provided they are biologically acceptable i.e. non-toxic under the conditions of treatment employed. These compounds may be identified using the methods described below.

The types of tissue that may be treated using the methods of the present invention include without limitation human and other mammalian muscle, tendons, ligaments, skin, mucosae, bone, cartilage, and cornea. The tissue may be damaged by surgical incisions, trauma, or other endogenous pathological processes, and healing may be inadequate due to systemic diseases such as liver failure, renal impairment, diabetes, peripheral vascular disease, or the administration of drugs that inhibit healing e.g. corticosteroids or immunosuppressive agents. Conversely, excessive healing may occur in arthiofibrosis (scar formation following surgery or injury to joints), heterotopic ossification (inappropriate bone formation), Ledderhosen's syndrome (Dupuytren's contracture of the feet), peritoneal adhesions, frozen shoulder, scieroderma, keloid formation, and excess scar formation in the skin, around surgically repaired tendons, and around surgical implants.

The active NOS stimulators, NONOates or NOS inhibitor compounds can be administered in conjunction with any pharmaceutically acceptable carrier known in the art, e.g. in sterile isotonic saline; creams or ointments such as those containing waxes, fatty acids, and propylene glycol; sprays; subcutaneous pumps; or slow-release formulations such as those containing polylactic acid-polyglycolic acid (PLAGA). It is contemplated that the concentrations that are locally effective in the rat system will approximate those that are effective in humans and other animals. Thus, the active compounds are formulated at concentrations ranging from about 0.1 mg/ml to about 5 mg/ml, preferably about 0.4 mg/ml. The pharmaceutical formulations of the present invention need not in themselves contain the entire amount of the agent that is effective in promoting or inhibiting healing, as such effective amounts can be reached by administration of a single application or dose, or a plurality of applications or doses of such pharmaceutical formulations.

In addition to the active compound, the formulation may comprise analgesics (e.g. lidocaine), antioxidants (e.g. superoxide dismutase, vitamin C, vitamin E) inhibitors of xanthine oxidase (e.g. allopurinol), corticosteroids, or combinations thereof.

NOS stimulators, NONOates, NOS inhibitors, or NO• scavengers may be administered topically or internally at the site of a wound, or applied during surgery. The only limitation on the route of administration is that the NO•-generating or NO•-inhibiting compounds must be available to increase or decrease the concentration of NO• in the vicinity of the damaged tissue for a sufficient period of time to enhance or inhibit wound healing, respectively. The NO•-generating or -inhibiting compounds may also be injected directly into damaged tissue, including intraarticular injection, or may be included in irrigation, lavage, or fluid used to distend and irrigate joints during arthroscopic surgery. In one embodiment, an NO•-generating compound is administered within 0–96 hours after trauma or surgery. In another embodiment, an NO•-generating agent is administered for a chronic condition e.g. ulceration, tennis elbow, jumper's knee, or a wound that has not healed.

Because NO• affects many physiological processes, for optimal use in practicing the present invention an agent should act locally i.e. within or in the immediate vicinity of a damaged tissue. In some cases, the anatomy of the affected tissue (e.g. a joint, or an area of skin) naturally restricts the activity of the agent to the damaged tissue or its immediate environment. In other cases, this restriction is achieved by employing a formulation (such as a cream, ointment, or slow-release polymer) that limits the diffusion of the agent, or by employing an agent with a relatively brief duration of activity.

In one embodiment, an NO•-inducing agent is formulated in a spray that is applied to the site of a wound or a surgical lesion.

In another embodiment, an NO-inducing agent is formulated as a gel, cream, or surgically implanted polymer, and used to treat ulcers, slow healing wounds, muscle injuries, tendon and ligament injuries, and fractures.

In another embodiment, an NO•-inhibiting agent is formulated in sterile saline and administered by injection to a local site of excessive healing.

MODEL SYSTEMS:

To identify different agents for use in the methods of the present invention, both a cell culture model and animal model may be employed.

Cell culture model: In cultured bovine chondrocytes, a Ca++-independent isoform of NOS can be induced by exposing the cells to *E. coli* lipopolysaccharide (endotoxin) for periods ranging from several hours to several days (see Example 2 below). Any cultured cell line which produces NO• in response to a stimulus car, be used. Cell homogenates are prepared at the appropriate times after exposure to test compounds. The level of NOS activity in the homogenates is assessed by measuring the conversion of $^3$H-L-arginine to $^3$H-L-citrulline (see Example 1). The level of NOS protein is measured immunochemically. For example, commercially available antibodies to NOS can be used in a radioimmunoassay or ELISA, using methods that are standard in the art. In this manner, both the absolute amount and the specific activity of NOS are determined. Furthermore, the production of NO• by cultured cells can be assessed by measuring the concentration of $NO_2^-$, a stable end-product of NO•, utilizing a spectrophotometric method based on the Greiss, reaction (Green et al., *Anal. Biochem.* 126:131, 1982).

Rat model system: The rat achilles tendon model is used to test model compounds for biological activity i.e. the ability to promote or inhibit wound healing in vivo. As, described in Example 1 below, one Achilles tendon in each rat is transsected surgically, and allowed to heal for periods ranging from 6 hours to 14 days. At each time point, the degree of healing is first assessed by measuring walking speed. The animals are then sacrificed and the tendons are excised and subjected to biomechanical testing and morphological and immunochemical analysis. NOS activity is measured in the excised tendons as above. Finally, body and muscle weight are monitored, and systemic and local toxicity are assessed by macroscopic and microscopic post-mortem examination. It will be understood by a skilled practitioner that any small mammal suitable for testing may be used, including rats, mice, rabbits, guinea pigs, and the like.

According to the present invention, agents that induce the production of NO• may be identified by the sequential use of the cell culture and animal model systems. Candidate compounds are first tested for their ability to cause a significant increase in NOS activity in the cell cultures i.e. at least 50% over the level present in the cell culture in the absence of the compound. Positive compounds are then administered to rats for several days prior to surgery, and administration is continued following surgery. Alternatively, the compounds are applied directly to the site during surgery. Test compounds that cause more rapid or more extensive healing, and exhibit little or no toxicity, are candidates for useful pharmacological agents. It will be understood by those skilled in the art that the preferred administration regimen for a given compound or treatment can be easily optimized by repeating the in vivo bioassay using different concentrations of the agent and different times of exposure.

A similar experimental protocol may be used to identify inhibitors of NO• production. In this case, the cell cultures are exposed to a stimulus that induces NOS, in the presence or absence of test compounds. Compounds that inhibit the increase in NO• production by at least 50% are then tested in vivo in the rat model for their ability to inhibit normal wound healing. A preferred inhibitory compound is Nw-nitro-L-arginine methyl ester (L-NAME), a structural analogue of L-arginine and a competitive inhibitor of ritric oxide synthase (see Example 1 below), which in the rat system is administered at a concentration of 1 mg/ml in the drinking water ad libitum for four days prior to surgery and throughout the post-operative period.

The following working examples are intended to serve non-limiting illustrations of the present invention.

EXAMPLE 1

An Animal Model System for The Role of NO in Wound Healing

The experiments described below were performed to determine if NOS activity is enhanced during wound healing in a rat model system, and to assess the effects of inhibiting NOS on tendon healing.

A. MATERIALS AND METHODS

Nicotinamide adenine dinucleotide phosphate (NADPH), calmodulin, valine, Nw-nitro-L-arginine methyl ester (L-NAME), Nw-nitro-D-arginine methyl estel (D-NAME), L-arginine, L-citrulline, β-NADPH, nitroblue tetrazolium, Triton X and Dowex 5OW anion exchange resin were obtained from Sigma Chemical Co., St Louis, Mo. NG-methyl-L-arginine monoacetate (L-NMMA) were obtained from Calbiocheim (Nottingham, UK). Bromphenol blue was purchased from BioRad Laboratories (Hercules, Calif.). L-(2,3,4,5-$^3$H) arginine hydrochloride was obtained from Amersharn (Buckinghamshire, UK). Tetrahydrobiopterin was obtained from B. Schirks Laboratories (Basel, Switzerland). Anti-nitric oxide synthase antibodies EC-NOS and mac-NOS were purchased from Transduction Laboratories, Lexington, Ky.

EXPERIMENTAL DESIGN

One hundred and twenty three outbred male Sprague-Dawley rats (Harlan Sprague Dawley Inc, Indianapolis, Ind.), weight 250–300 g were utilized for testing for nitric oxide synthase activity, histological and immunohistochemical evaluation, and nitric oxide synthase inhibition experiments. NOS activity was determined at 6 hrs (n=8), 1 day (n=8), 7 days (n=8) and 14 days (n=8) in both the surgically divided and uninjured Achilles tendon. Immunohistochemistry and histological evaluation of uninjured and surgically divided Achilles tendons was performed at day 1 (n=2), day 4 (n=2), day 7 (D-NAME, n=6; L-NAME, n=6), and day 14 (n=2).

In the following NOS inhibition experiments, animals were fed the indicated chemicals at 1 mg/ml in their drinking water ad libitum for four days prior to surgical division of the right Achilles tendon and throughout the post-operative experimental period, with the exception of experiment (c)*, where the drugs were given from the immediate post-operative period:

(a) 1 week D-NAME (n=9) vs L-NAME (n=11); walking speed and biomechanical analyses at day 7.

(b) 2 weeks water (n=4) vs L-NAME (n=4); morphological and histological analyses at day 14.

(c) 2 weeks D-NAME (n=6), L-NAME (n=4), L-NAME+ L-citruiline (n=5)*; walking speed assessments at day 8 and 15, biomechanical analyses at daly 15.

(d) 3 weeks D-NAME (n=8), L-NAME (n=8), L-arginine (n=8), walking speed assessments at days 1,4,8,11,15, 18,22, biomechanical assessment, muscle weight and autopsy at day 22.

L-NAME (Nw-nitro-L-arginine methyl ester) is a structural analogue of L-arginine and is a competitive inhibitor of nitric oxide synthase. D-NAME (Nw-nitro-D-arcinine methyl ester) is its enantomer, which fails to inhibit nitric oxide synthase (control). L-arginine was used as a potential positive control, since if Larginine were in relative short supply, NO• synthesis from nitric oxide synthase might be enhanced by the addition of L-arginine. The combination of L-NAME and L-citrulline was used as a control to monitor the potential effects of L-citrulline depletion.

SURGICAL PROCEDURES

The rats were housed in beta-chip-lined plastic cages, two animals per cage, with a 12-hour light, 12 hour dark cycle in an animal care facility and fed rat chow and waiter ad libitum. Anaesthesia was achieved by intraperitoneal injection of 80 mg/kg ketamine (Park Davis, Morris Plains, N.J.) and 5 mg/kg xylazine (Miles Inc, Shawnee Mission, Kans.). All surgical procedures were performed under sterile, conditions with the aid of 2.5× microsurgical loops. The surgical procedure was similar to that previously outlined. A 3 cm midline incision was made over the right Achilles tendon and the Achilles tendon and plantaris were isolated from the surrounding fascia. The underlying fascia was disrupted by spreading with a pair of small straight scissors. The tendinous portion of the plantaris was removed and the, Achilles tendon was divided cleanly in its mid-substance, 0.5 cm from its calcaneal insertion with a scalpel. The skin was then sutured with two simple nylon sutures of 5-0 ethilon monofilament nylon on a PC-1 cutting needle (Ethicon Inc, N.J.). No operation was performed on the left, uninjured, hind limb. No cast or dressings were applied and the animals were unrestricted during the healing phase. The animals were sacrificed be $CO_2$ inhalation.

WALKING SPEED ASSESSMENT

The animals were tested in a confined walkway with a dark shelter at the end. Each rat was held by its chest at the start of the walkway and then allowed to walk/run to the dark shelter at the end of the walkway. The time taken for the rat to cover the first half (21.5 cm) and the total length (43 cm) of the walkway was measured by individuals blinded to the treatment groups.

BODY AND MUSCLE WEIGHT

All animals were weighed prior to surgery, at weekly intervals, and at sacrifice. After sacrifice the right triceps of rats fed D-NAME (n=8), L-NAME (n=8) or L-arginine (n=8) for three weeks was harvested, weighed for wet weight, lyophilized for dry weight and the water content calculated.

BIOMECHANICAL TESTING

One hundred and fifty two harvested lower limbs were placed in phosphate buffered saline (PBS), frozen and stored at −70° C. for an average of seven days prior to testing. On the day prior to testing the specimens were thawed. All extraneous soft and hard tissues were removed by blunt and sharp dissection from the Achilles tendon, formerly intramuscular tendinous fibers and the hind foot. Area measurements of the uninjured and sham operated tendons were made with an area micrometer (Mitutoyo, Tokyo, Japan). Length measurements, were made with a 0.02 mm calibrated caliper (Draper, Japan). The formerly intramuscular tendinous fibers were then secured between two strips of white labelling tape with Thick Gel Super Glue® (Super Glue Corporation, N.Y.) such that the distal edge of the tape was 1.0 cm from the calcaneal insertion. The calcaneus was fixed at 45° in an adjustable rubber-gripped clamp (Panavise, Sparks, N.V.). Throughout the procedure care was taken to ensure that neither the Super Glue® nor the self curing plastic contaminated the tendon proper and the specimens were kept moist by application of PBS. Mechanical testing was carried out using a MTS 810 material test system (MTS Systems Corporation, PN). Each specimen underwent a constant velocity ramp to failure test at 1 cm/sec (≈100%/sec). Voltage-time and displacement-time histories for each test were transferred to a 486/33C computer (Gateway 200, North Sioux City, S.Dak.) for subsequent data analysis. At the completion of testing, each specimen was inspected for type of failure, i.e. substance tear versus avulsion.

MORPHOLOGY AND IMMUNIOHISTOCHEMISTRY

Experimental and uninjured Achilles tendons were immediately placed in 5% polyvinyl alcohol for one hour, frozen in liquid nitrocen and stored at −70° C. Coronal cryostat sections of the mid-substance of the Achilles tendons were cut at 5 μm, stained with Hematoxylin and Eosin, and examined by individuals blinded to the treatment group. Direct immunofluorescence staining was performed utilizing antibodies to human macrophage nitric oxide synthase (mac-NOS) and endothelial nitric oxide synthase (EC-NOS), purified from mouse ascites in a dilution of in 1:500 in phosphate buffered saline (PBS), and fluorescent labelled goat IgG A and M (Cappell, N.Y.) diluted 1:100 in PBS. The slides were then mounted and examined and photographed under direct immunofluorescence with an Aiophot Immunofluorescence Microscope (Zeiss, Oberkochen, Germany).

NITRIC OXIDE SYNTHASE ASSAY

Immediately after sacrifice both the left (un-injured) and the right (previously surgically divided) Achilles tendons were harvested at 6 hrs, 24 hrs, 7 and 14 days after surgery (n=8 for each group) and quickly frozen in liquid nitrogen Samples were homogenized on ice using an Ultra-Turrax T 25 homogenizer (Janke & Kunkel, IKA Labortechnik, Staufen I, Br., Germany) in a homogenization buffer composed of: 50 mM Tris-HCl, 0.1 mM EDTA, 0.1 mM EGTA, 12 mM 2-mercaptoethanol and 1 mM phenylmethylsulfonyl fluoride (pH 7.4).

Conversion of $^3$H-L-arginine to $^3$H-L-citrulline was measured in the homogenates as described. Briefly, each cell homogenate (40 μl) was incubated in the presence of $^3$H-L-arginine (10 μM, 5 kBq/tube), NADPH (1 mM), tetrahydrobipterin (5 μM), valine (50 mM), calcium (2 mM) and calmodulin (30 nM) for 30 min at 370° C. in HEPES buffer (pH 7.5). The reaction was stopped by dilution with 1 ml of ice cold HEPES buffer (pH 7.5) containing EGTA (2 mM) and EDTA (2 mM). Reaction mixtures were applied to Dowex 5OW ($Na^+$ form) columns and the eluted $^3$H-L-citrulline activity was measured by scintillation spectroscopy (Beckman, LS3801; Fullerton, Calif., USA).

Experiments performed in the absence of calcium and in the presence of EGTA (5 mM) determined the calcium-independent NOS activity. Parallel experiment in the presence of calcium and L-NMMA (3 mM) determined the extent of detection and/or formation of $^3$H-L-citrulline that was independent of specific NOS activity, and this was subtracted from all values. The data represent means of two independent determinations, each of them performed in quadruplicates using pooled tendon samples from 4—4 rats in each experimental group.

STATISTICAL ANALYSIS

All values in the text and figures are expressed as mean±standard error of the mean of n observations. Statistical analysis between experimental groups was performed using unpaired two-tailed Student's t tests. Statistical analysis between the right surgically divided and the left uninjured were performed using paired two-tailed Student's t tests. The confidence limit was predetermined at an alpha level of 0.05.

B. RESULTS

EFFECTS OF SURGERY

The macroscopic appearance of uninjured tendons was that of glistening, pearly-white, longitudinally arranged structures 1 cm long, and 2.5–3.0 mm$^2$ in cross-section. In contrast, all tendons previously subjected to surgical division were opaque structures 10–17 mm long and 6–10 mm$^2$ in cross-sectional area. At the microscopic level, uninjured tendons consisted of dense, parallel bundles of homogeneous eosinophilic substance aligned with the long axis of the tendon. Interspersed within this matrix were a few longitudinally arranged spindle and oval shaped fibroblasts with prominent nuclei and sparse cytoplasm.

In the divided Achilles tendons, the area between the cut ends of the tendon initially was filled with a loose connective tissue matrix containing numerous inflammatory cells (neutrophils, basophils, macrophages and lymphocytes) and erythrocytes. Over 15 days this loose connective tissue matrix was replaced by a more homogeneous, denser eosinophilic matrix. Plump fibroblasts with large nuclei were the predominant cell type, and were aligned in the longitudinal axis of the tendon. The junction between the old tendon and the new matrix was characterized by a dense (0.1 mm) band of oval shaped fibroblasts with little organization. With time, the tendon-new matrix interface and the band of disorganized fibroblasts; became less distinct. The collagenous tissue also became more organized, with fewer fibroblasts and more matrix.

NITRIC OXIDE SYNTHASE ACTIVITY

Figure 2:
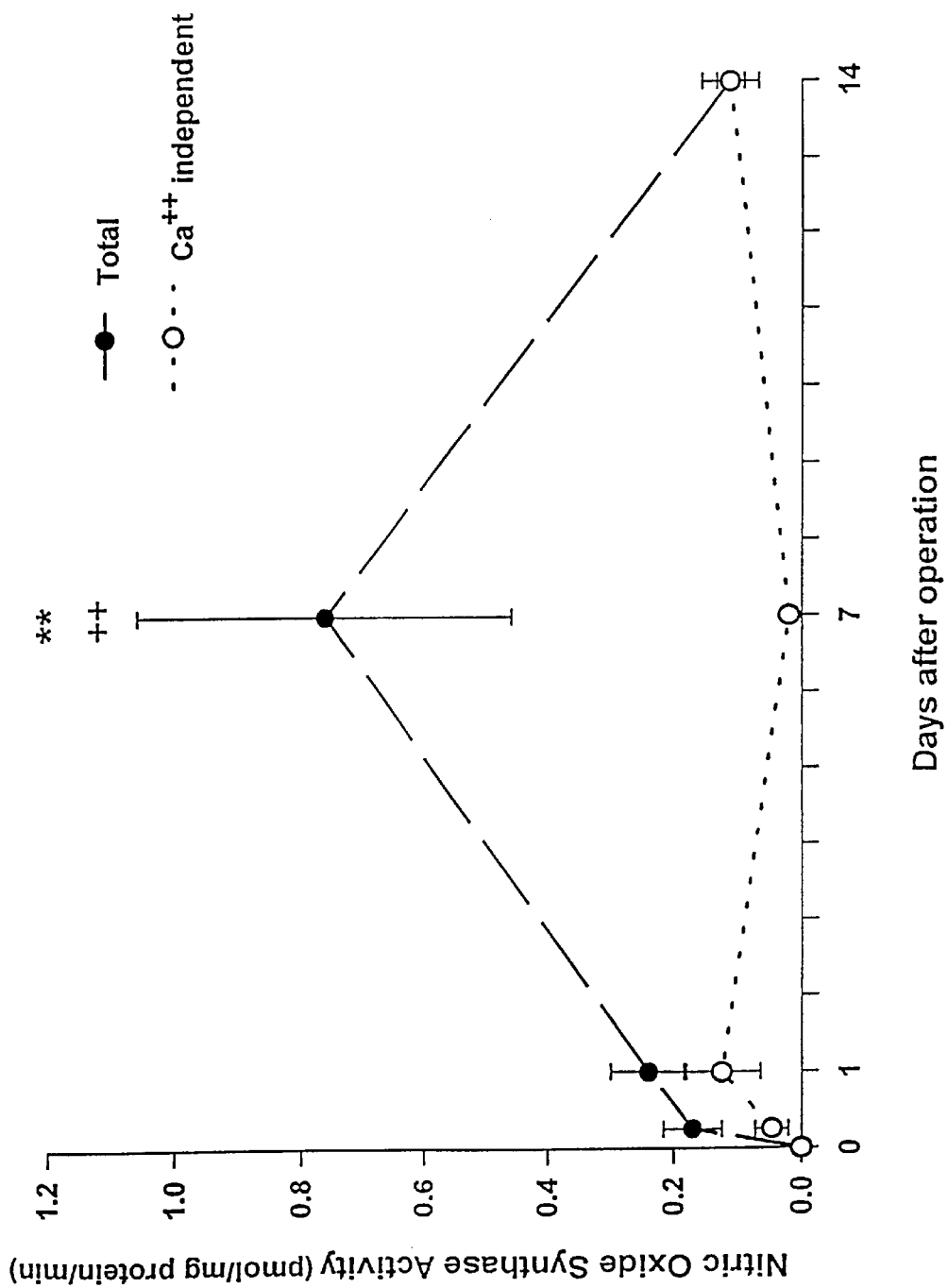
FIG. 2 shows the time course of total and Ca- independent nitric oxide synthase activity in surgically divided rat Achilles tendons. Mean ±SEM of two independent determinations, each of them performed in quadruplicates using pooled tendon samples from 4+4 rats in each experimental group. **=$p<0.01$ when compared with the uninjured side, ++=$p<0.01$ when compared with the other time points; unpaired two-tailed Student's t tests.

In uninjured tendon samples, very low $Ca^{++}$-dependent and negligible $Ca^{++}$-independent nitric oxide synthase activity was detected. At 6 hrs and 24 hrs post surgery there was a slight increase in $Ca^{++}$-dependent and $Ca^{++}$-independent nitric oxide synthase. By day 7, there was a five-fold increase in $Ca^{++}$-dependent nitric oxide synthase activity (FIG. 2). At the same time point, no $Ca^{++}$-independent NOS activity was found. At day 14, NOS activity had returned to near normal. The majority of NOS activity at day 14 was, however, $Ca^{++}$-independent. There were no changes in NOS activity at any of these time points in the uninjured contralateral side (not shown).

IMMUNOHISTOCHEMISTRY

Sections prepared with the secondary antibody alone, or after 24 hours formaldehyde fixation, showed no immunofluorescence. The intimal cells of blood vessels consistently reacted strongly to EC-NOS and less strongly to mac-NOS in both uninjured tendon and healing tendon. Gastrocnemius and soleus muscle reacted strongly and diffusely to EC-NOS and mac-NOS in both uninjured and healing Achilles tendons. The tendon fiber bundles and fibroblasts within the tendon matrix of uninjured tendons showed no immunofluorescence. This contrasted with the tissue that filled the defect in the Achilles tendon. This tissue reacted strongly to both EC-NOS and mac-NOS. The intensity and number of fibroblasts reacting to NOS antibodies was greatest at day 7. The intensity and distribution of immunofluorescence to mac-NOS and EC-NOS in this healing tissue was slightly different. EC-NOS was distributed diffusely throughout all the fibroblasts within the healing tendinous tissue, often with the greatest intensity at the edges of the cells. Fibroblasts reacting to mac-NOS had a more heterogeneous pattern of immunofluorescence, with some fibroblasts staining very brightly and others less so The uninjured tendon fibers had minimal immunofluorescence to EC-NOS and mac-NOS through the whole healing period.

NITRIC OXIDE SYNTHASE INHIBITION

Tendon Morphology

Figure 3:
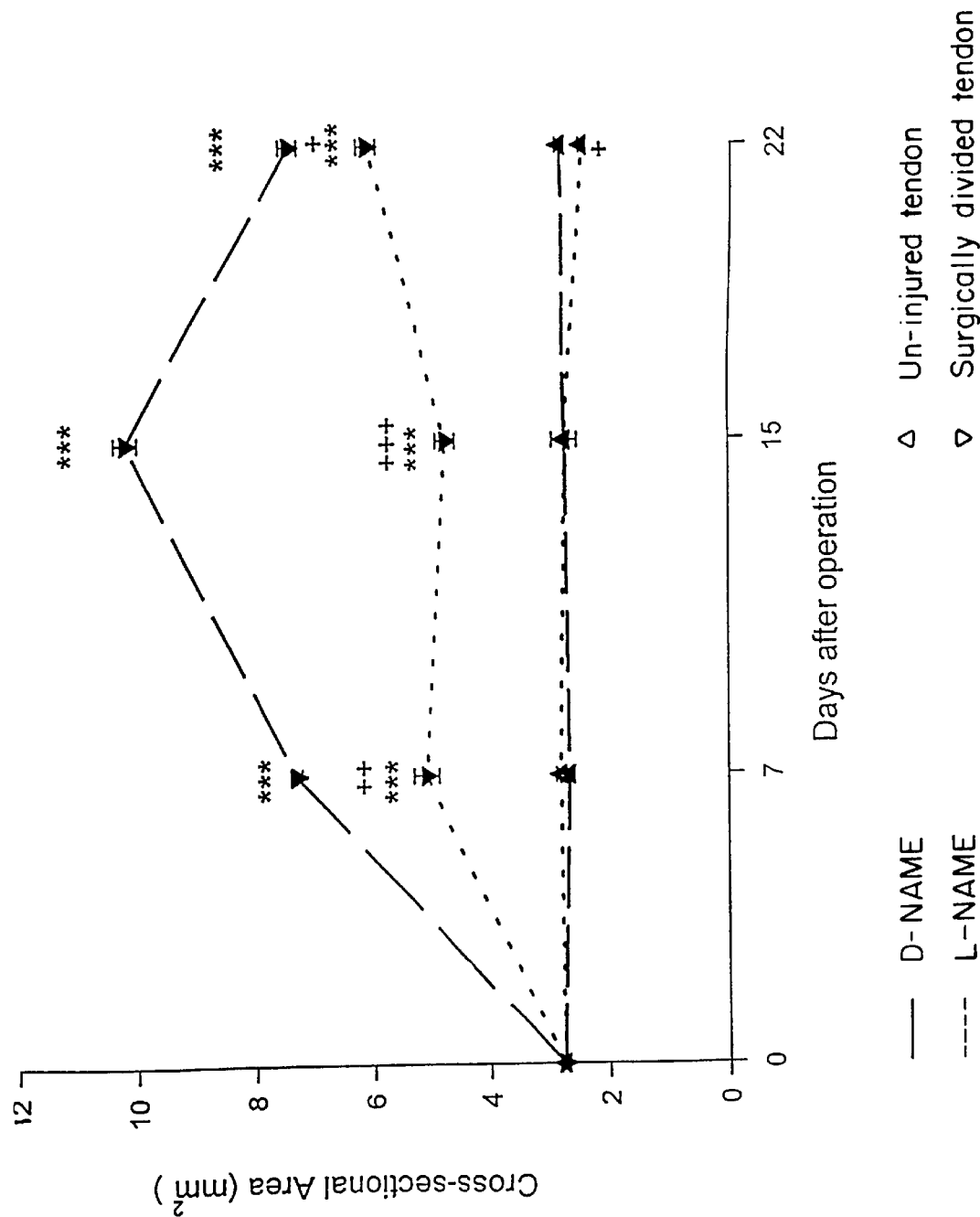
FIG. 3 shows the time course of a cross-sectional area of uninjured and surgically divided Achilles tendons in rats fed the nitric oxide synthase inhibitor Nw-nitro-L-arginine methyl ester (L-NAME) or its inactive enantomer Nw-nitro-D-arginine methyl ester (D-NAME). Mean±SEM. n=11,9; 4,4; 8,8 for D-NAME, L-NAME at day 7; 15; 22.<0.001 when compared with the uninjured side; paired two-tailed Student's t tests. +=$p<0.05$, ++=$p<0.01$, +++=$p<0.001$ when compared with the control (D-NAME) group; unpaired two-tailed Student's t tests.

Inhibition of nitric oxide synthase by the L-arginine analogue Nw-nitro-L-arginine methyl ester (L-NAME) given orally four days prior to surgery and throughout the experimental period inhibited the cross-sectional area of healing Achilles tendon by 30% at day 7 ($p<0.01$), 50% at day 15 ($p<0.001$) and 17% at day 22 ($p<0.05$) (FIG. 3). Within the healing tendons the cut ends of the tendon were separated by 5–8 mm, a distance that did not change with healing time or with the administration of L-NAME or L-arginine (not shown).

Light Microscopy

Apart from the decrease in cross-sectional area of the healing tendon of rats fed L-NAME, there were no subjective differences in the microscopic appearance of the healing tissue in L-NAME versus D-NAME fed rats.

Biomechanics

All load-deflection curves were non-linear and showed a stiffening response (increasing load with increasing deformation). The failure site of all uninjured tendons was at the distal tendon-calcaneus interface. In the previously divided tendons, failure occurred at both the proximal clamp-tendon interface, the mid-substance and the tendon-calcaneal interface. The majority of failures at the early time points were in the mid-substance. At day 22 many failures in the healing tendon occurred at the clamp-tendon interface and by avulsion of the tendinous fibers from the proximal fixation. For this reason the failure load data for the healing tendons at day 22 was disregarded. The healing Achilles tendon constructs had a greater toe displacement, maximum displacement, and had a lower ultimate failure load at day 7, 15 and 22 than uninjured tendon constructs. These differences decreased with healing time (not shown).

Figure 4:
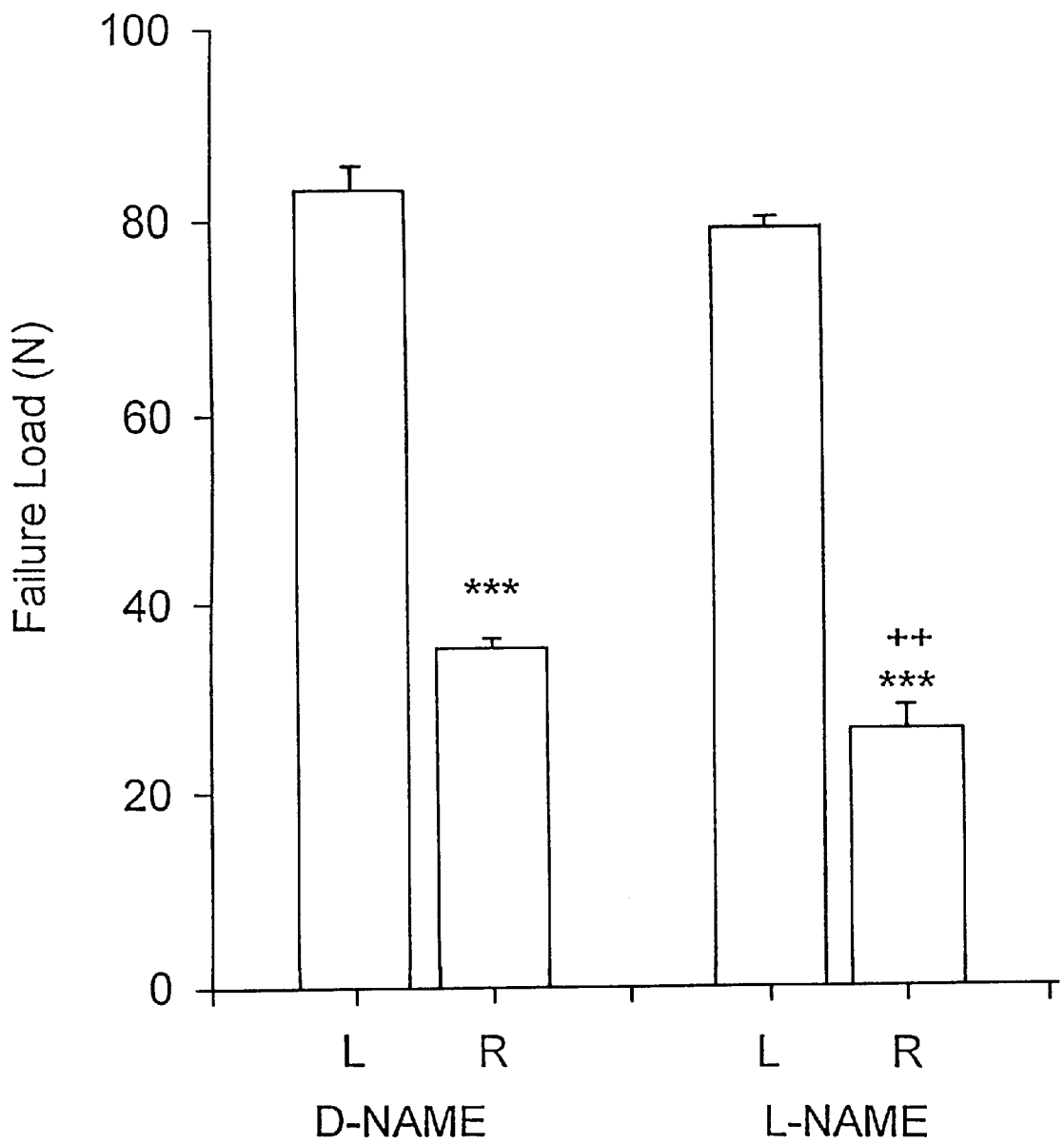
FIG. 4 shows the ultimate failure load of Achilles tendon constructs of rats fed the nitric oxide synthase inhibitor Nw-nitro-L-arginine methyl ester (L-NAME) or its inactive enantiomer Nw-nitro-D-arginine methyl ester (D-NAME) at day 7. R=surgically divided, L=uninjured Achilles tendon. Mean±SEM, n=11 (D-NAME), n=9 (L-NAME). ***=$p<0.001$ when compared with the uninjured side; paired two-tailed Student's t tests. ++=$p<0.01$ when compared with the control (D-NAME) group; un-paired two-tailed Student's t tests.

Inhibition of nitric oxide synthase activity with L-NAME caused a 24%, reduction in failure load on the formerly divided side ($p<0.01$) on day 7. The uninjured Achilles tendon constructs were unaffected by L-NAME ingestion (FIG. 4). Inhibition of nitric oxide synthase did not affect toe displacement, maximum displacement, stiffness, energy, modulus or maximum stress of the healing tendons of the surgically divided or uninjured Achilles constructs (not shown.)

Weight

Figure 5:
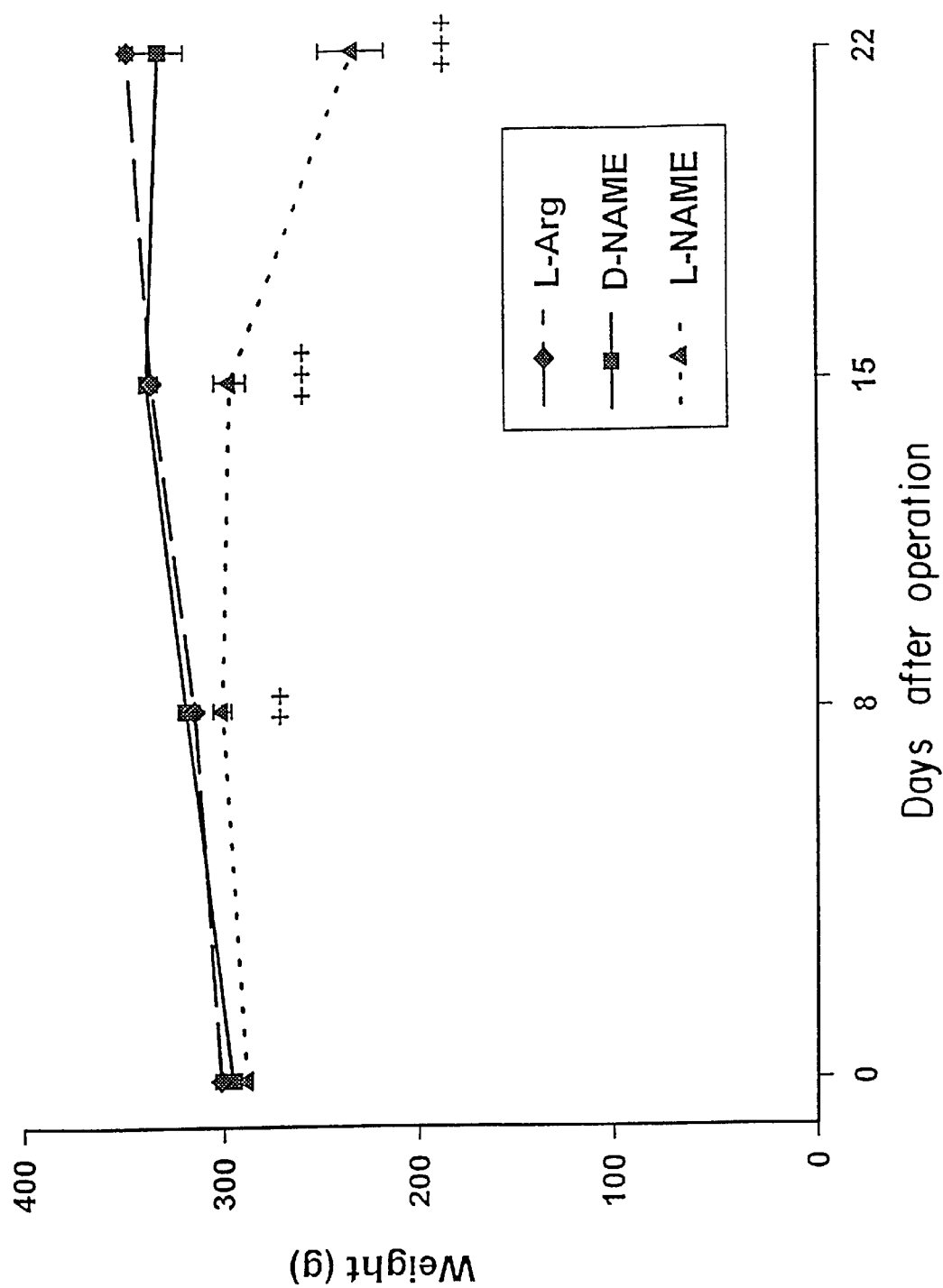
FIG. 5 shows the weight of rats fed the nitric oxide synthase inhibitor Nw-nitro-L-zirginine methyl ester (L-NAME) or its inactive enantomer Nw-nitro-D-arginine methyl ester (D-NAME) or L-arginine (L-arg). Mean SEM, n=8 for each group. +++=$p<0.001$ when compared with the control (D-NAME) group; unpaired two-tailed Student's t tests.

Rats fed the nitric oxide synthase inhibitor L-NAME either failed to gain weight or lost weight over the first 15 days of treatment, and by day 22 the rats were 30% lighter than their initial preoperative weight ($p<0.001$; FIG. 5). This contrasted to rats fed the same dose of D-NAME or L-arginine, who all increased their weight by 30% over 22 days.

Muscle Weight

Figure 6:
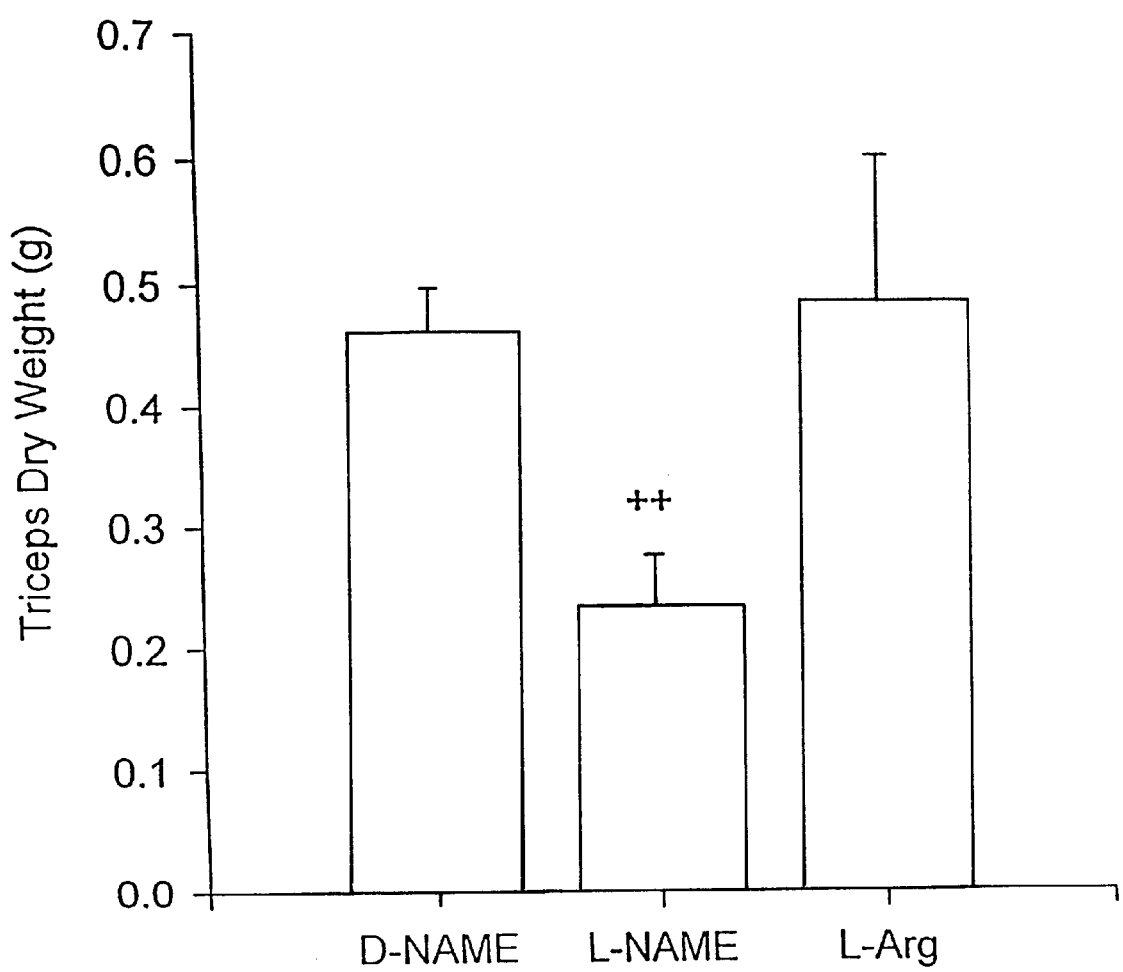
FIG. 6 shows the effects of nitric oxide synthase inhibition on muscle dry weight in rats fed the nitric oxide synthase inhibitor Nw-nitro-L-arginine methyl ester (L-NAME) or its inactive enantomer Nw-nitro-D-arginine methyl ester (D-NAME) or L-arginine (L-arg). Mean±SEM, n=8 for each group. ++=$p<0.01$ when compared with the control (D-NAME) group; unpaired two-tailed Student's t tests.

Inhibition of nitric oxide synthase resulted in a 30% loss in wet weight and 40% loss in dry muscle weight at day 22 ($p<0.01$). L-arginine had no effect (FIG. 6).

Walking Speed

Figure 7A:
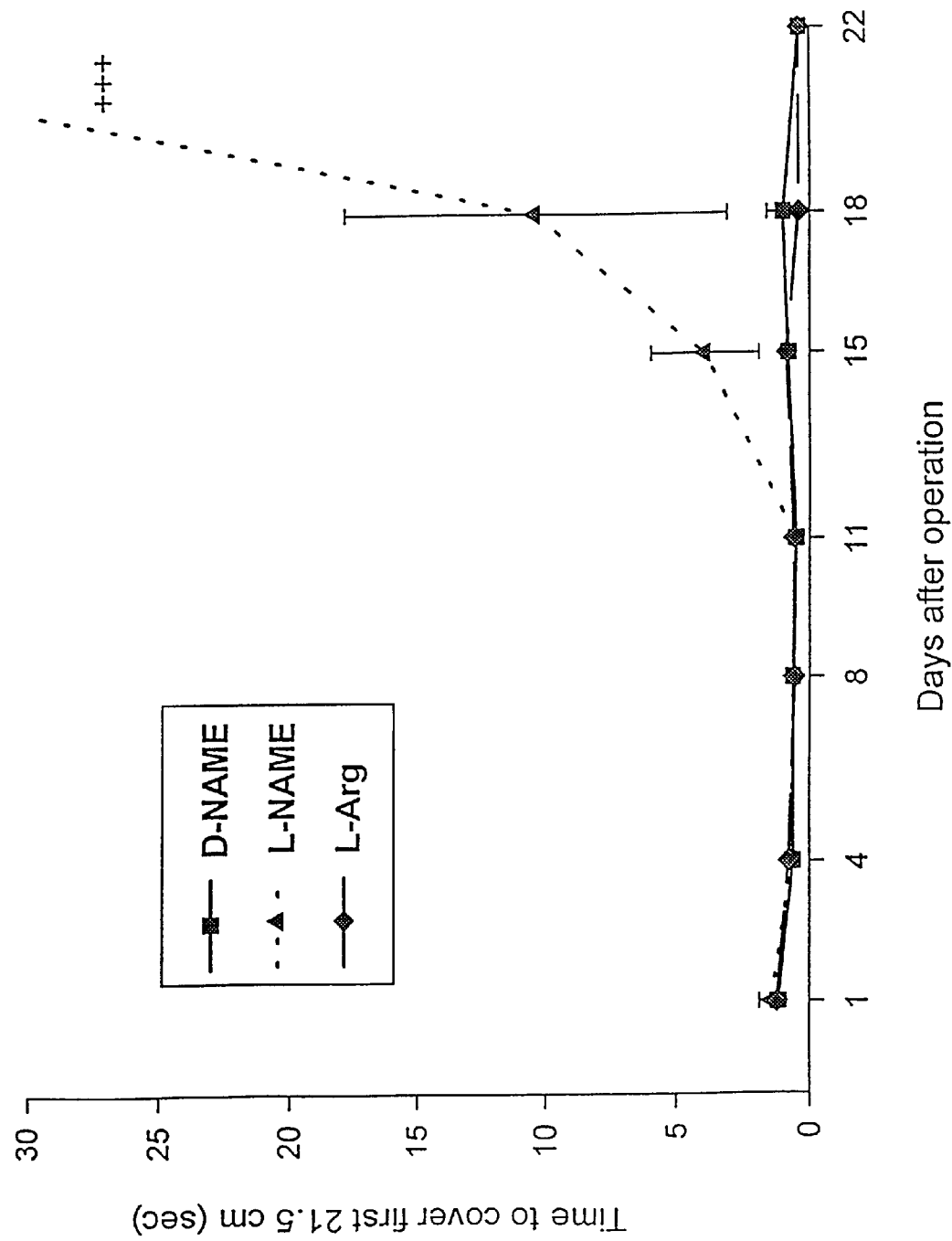
FIGS. 7a and 7b show the time course of the effects of nitric oxide synthase inhibition on walking speed down the first half (FIG. 7a) and second half (FIG. 7b) of a confined walkway. Rats were fed the nitric oxide synthase inhibitor Nw-nitro-L-arginine methyl ester (L-NAME) or its inactive enantomer Nw-nitro-D-arginine methyl ester (D-NAME) or L-arginine (L-arg). Mean–+SEM, n=8 for each group. +=$p<0,05$, +++=$p<0.001$ when compared with the control (D-NAME) aroup; unpaired two-tailed Student's t tests.
Figure 7B:
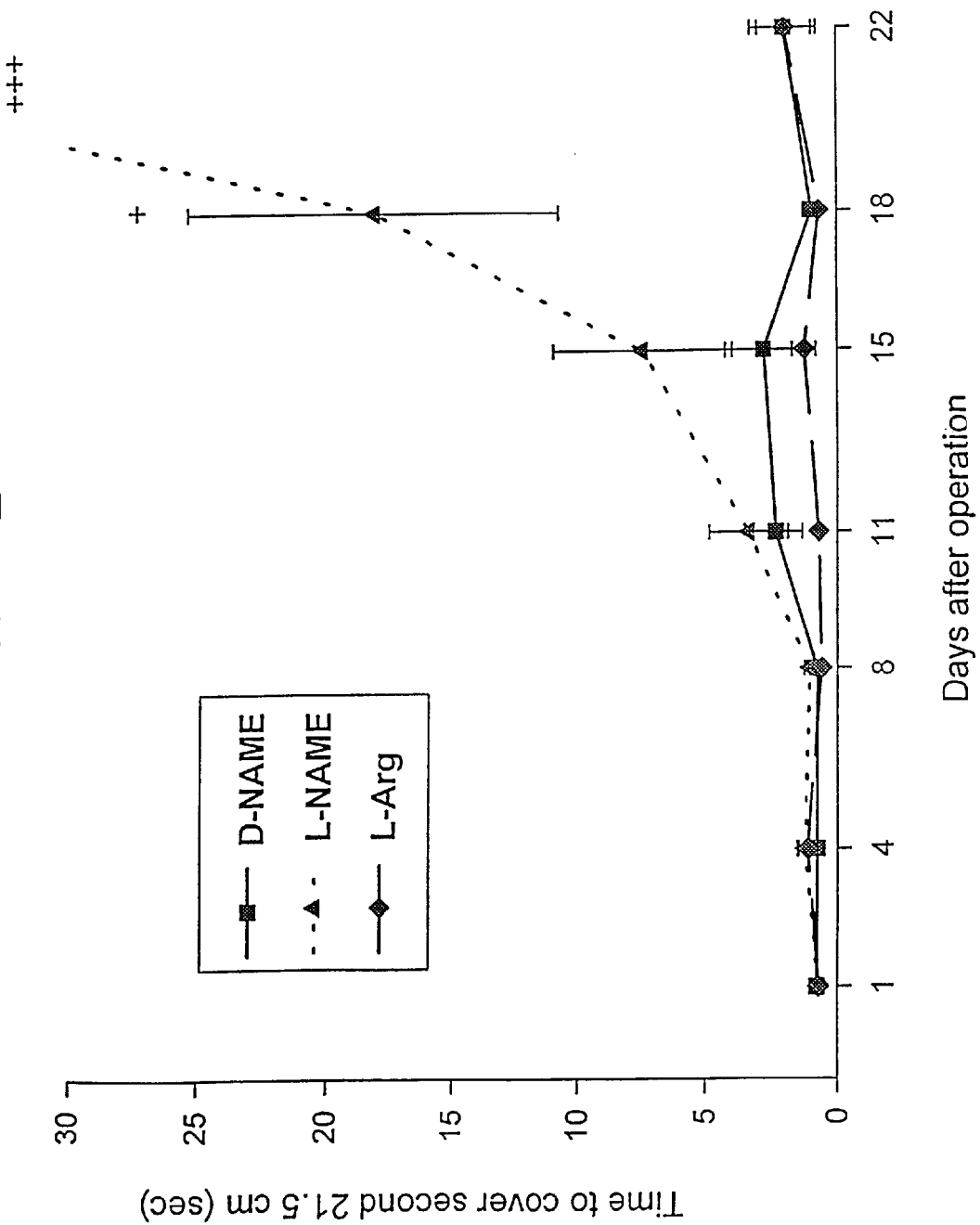

There were no changes in behavior or walking speed of nitric oxide synthase inhibited rats during the first week of treatment. After day 11, L-NAME fed rats were progressively quieter, slower (FIGS. 7a and 7b) and more reluctant to walk down a confined walkway. L-NAME fed rats were especially reluctant to walk down the second part of the walkway into the dark shelter (FIG. 7a versus 7b).

Other Systemic Effects

From day 15, L-NAME fed rats became progressively unwell. Four out of the eight rats in this group developed motor palsies of either the upper limbs (n=1) or lower limbs (n=2). All L-NAME fed rats lost coat texture and developed periorbital rubor. ⅝ developed severe dyspnoea. Two died on day 21, and the whole experiment was shorted to 22 days rather than the planned 28 days. At post mortem examination all L-NAME fed rats had scant body fat, empty small intestines, myocardial lesions consistent with infarction and granular kidneys. The D-NAME and L-arginine fed rats failed to display any of the above changes.

L-citrulline

One concern was that these systemic effects were secondary to a L-citrulline deficiency induced by nitric oxide synthase inhibition rather than a lack of NO, activity. For this reason, a group of rats were fed both L-NAME and L-citrulline and compared with a L-NAME group and a D-NAME group. L-NAME/L-citrulline fed rats lost weight and walking speed at the same rate as rats fed L-NAME alone (FIGS. 8a and 8b); implicating a NO deficiency rather than a L-citrulline deficiency as the underlying reason for the systemic effects of L-NAME.

Post-Injury Nitric Oxide Synthase Inhibition

Figure 8A:
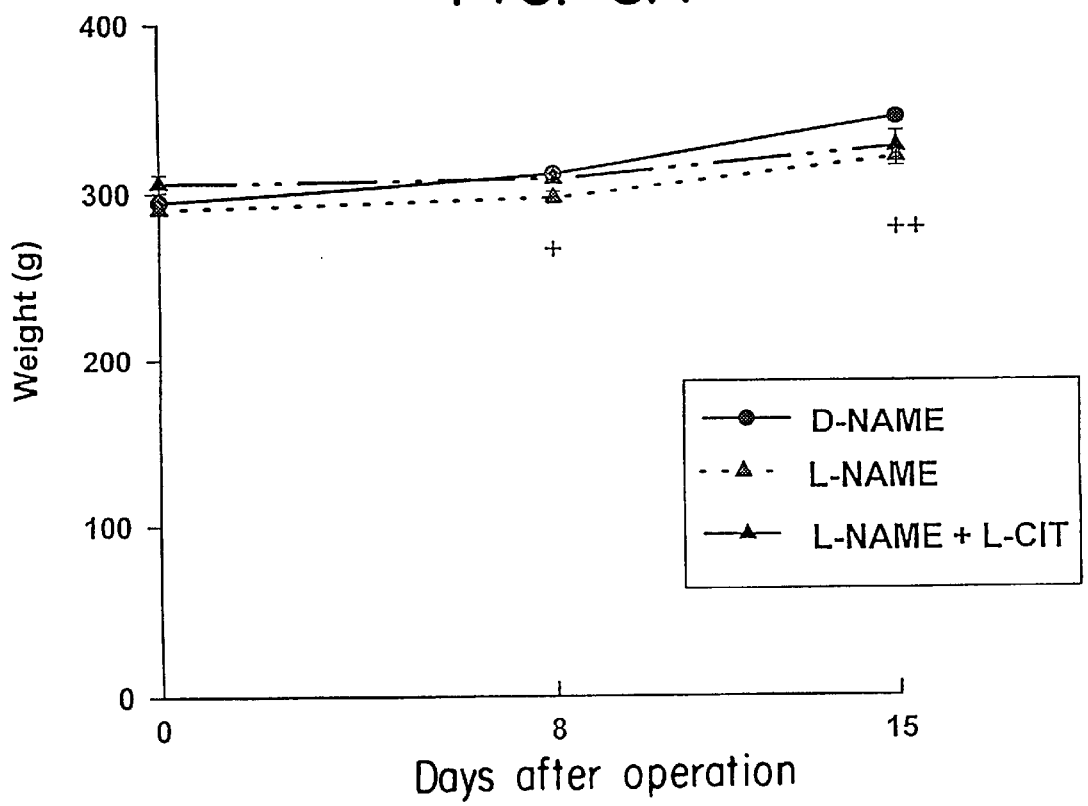
FIG. 8a and 8b show a time course of weight (FIG. 8a) and walking speed (FIG. 8b) of rats fed the nitric oxide synthase inhibitor Nw-nitro-L-arginine methyl ester (L-NAME) or its inactive enantiomer Nw-nitro-D-arginine methyl ester (D-NAME) or L-NAME+L-citrulline (L-CIT). Mean'±SEM, n=6,5,5 for each group. +=$p<0.05$, +++=$p<0.001$ when compared with the control (D-NAME) group; unpaired two-tailed Student's t tests.
Figure 8B:
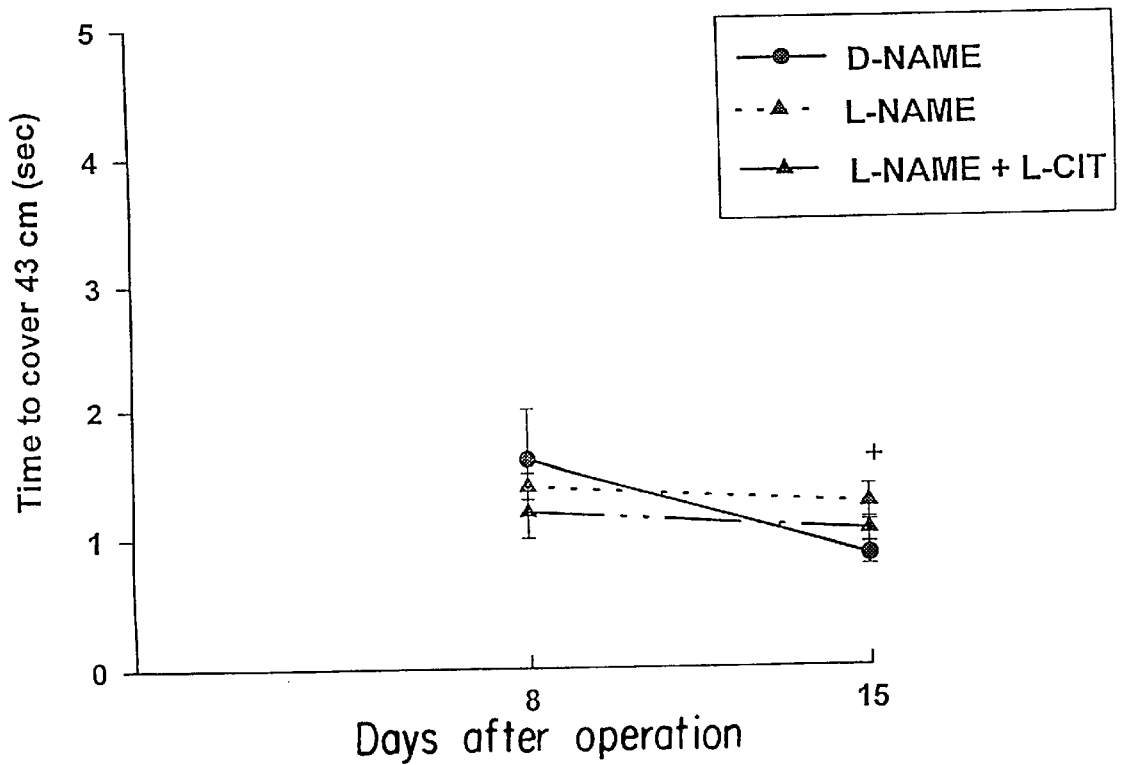
Figure 9A:
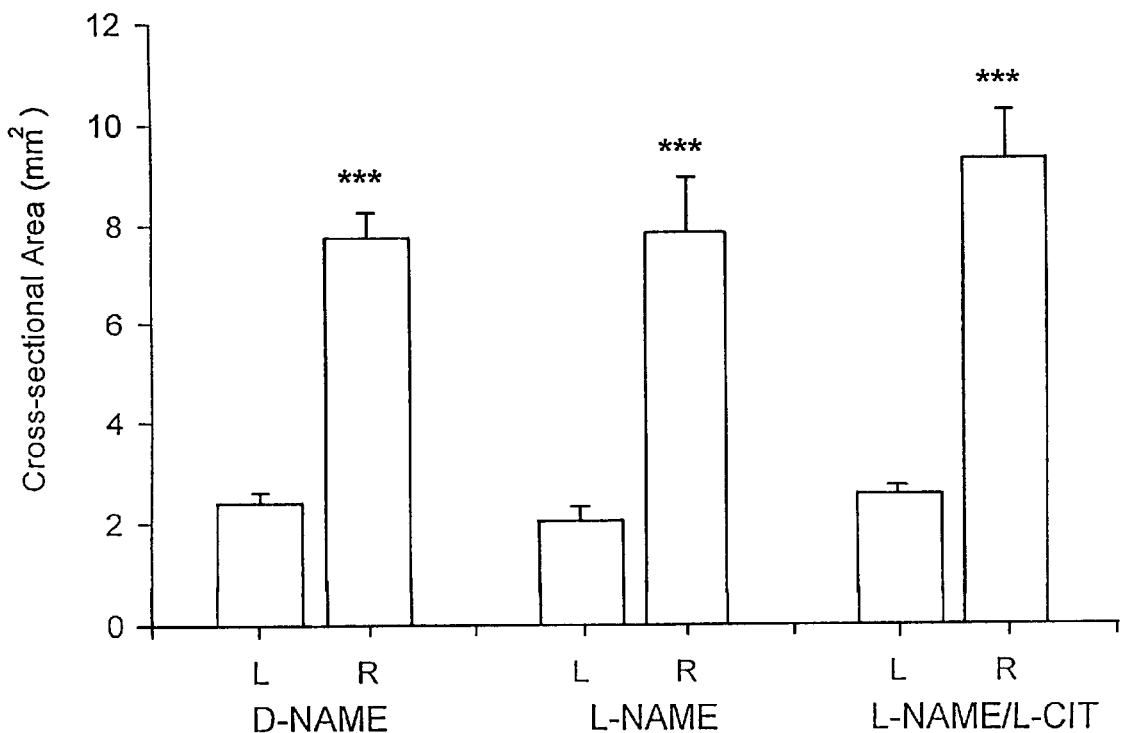
FIG. 9a and 9b show the cross-sectional area (a) and ultimate failure load (b) of Achilles tendon constructs 15 days after surgical division (R) and in the uninjured (L) Achilles tendon constructs of rats fed the nitric oxide synthase inhibitor Nw-nitro-L-arginine methyl ester (L-NAME) or its inactive enantiomer Nw-nitro-D-arginine methyl ester (D-NAME) or L-NAME+L-citrulline (L-CIT). Mean±SEM, n=6,5,5 for each group. ***=$p<0.001$ when compared with the uninjured side; paired two-tailed Student's t tests.
Figure 9B:
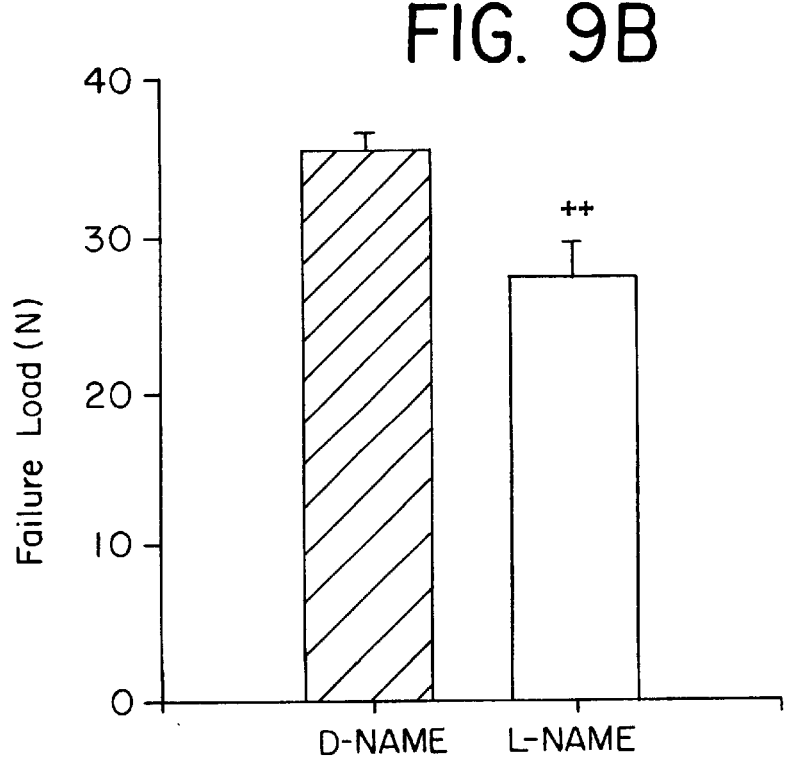

The role of nitric oxide synthase in initiating the healing response in divided Achilles tendon was assessed by feeding rats L-NAME from the immediate post-operative period, rather than for four days preoperatively. With this regimen, the L-NAME fed rats displayed the usual systemic changes at day 15 (weight loss and loss of walking speed; FIGS. 8a and 8b), but failed to show any changes in tendon cross-sectional area (FIG. 9a) or failure load (FIG. 9b).

C. DISCUSSION

NOS activity was induced during rat Achilles tendon healing. The increased activity was predominantly in fibroblasts within the healing tissue, was maximal at day 7, and returned to baseline activities at day 14. Inhibition of NOS prior to injury inhibited the magnitude of the healing response (tendon cross-sectional area and failure load). Inhibition of NOS after injury did not alter the healing response. Systemic inhibition of NOS for more than two weeks resulted in weight loss, muscle mass loss, psychological changes, loss in walking speed and eventually paralysis.

These findings have several important implications for the present invention. First, NO plays an important role in the initiation of wound healing. Second, agents that inhibit NO production can be used to selectively suppress healing processes when such processes are deleterious. Third, the methods and compositions of the present invention must be locally effective to avoid systemic effects of NO stimulation or inhibition.

This experiment also taught that proliferating fibroblasts within the healing tendon accounted for most of the new NOS immunofluorescence at day 7 post-surgery, and biochemical assays demonstrated that the new NOS was primarily Ca-dependent. This supports the use of a cell culture system to induce Ca-dependent NOS as described above.

EXAMPLE 2

Endotoxin-Induced NO• Release From Cultured Bovine Chondroctyes

Chondrocytes were obtained from slices of bovine hindfoot articular cartilage or bovine articular occipital cartilage by collagenase digestion as follows: the slices were incubated in 0.25% (w/v) collagenase (Sigma Chemical Co., St. Louis, Mo.), 1% aritibiotic-antimycotic solution, 2% (v/v) HEPES with vigorous agitation at 37° C. for six hours. The cell suspension was then centrifuged at 30,000 rpm for 10 min and the supernatant discarded. The cells present in the pellet were resuspended in fresh growth medium (medium 199 or Dulbecco's MEM supplemented with 10% fetal bovine serum) and plated in 75 mm culture flasks.

The production of NO• by these cells was assessed by measuring the concentration of $NO_2^-$, a stable end-product of NO•, utilizing a spectrophotometiric method based on the Greiss reaction (Green et al., *Anal.Biochem.* 126:131, 1982). The absorbance was measured at 550/650 nm with a 340 ATTC microplate photometer (Tecan US Inc., Research Triangle Park, N.C.).

No constitutive release of $NO_2^-$ was detected in these cultures. However, addition of 1 μg/ml *E. coli* endotoxin, or of the inflammatory mediators IL-1β and TNF-α, resulted in the release of 100 nmol $NO_2^-$/106 cells/24 hours. The induction of $NO_2^-$ by endotoxin was dose- and time-dependent, with maximal stimulation at 24 hours. $NO_2^-$ production was completely inhibited by L-NAME, confirming nitric oxide synthase as the source for $NO_2^-$ (and, by inference, NO•). The induction of $NO_2^-$ in chondrocytes by endotoxin was not inhibited by EGTA, indicating that the nitric oxide synthase in these cells is not $Ca^{++}$-dependent.

EXAMPLE 3

Therapeutic Administration of an NO• Inducer

Following are clinical situations in which NO• inducers or NONOates may be administered to promote wound healing.

A. Ruptured Achilles Tendon: Surgical repair of a ruptured Achilles tendon involves making a midline incision over the Achilles tendon, isolating the ends of the ruptured tendon, and re-apposing the ends of the tendon with a #1 Ethibond suture configured in a Kessler-type fashion. At the time of surgery, a polyethyleneimine cellulose/NO• inducer adduct is mixed with a superabsorbent polymer (Waterlock), prepared by mixing 0.5 g Waterlock with 50 ml sterile water, followed by addition of 0.4 g of an NO• inducer or NONOate. This mixture is carefully applied around the edges of the re-apposed tendon and in any defects between the tendon edges. This polymer is predicted to, release NO• at a constant rate over a 7-day period.

B. Chronic Skin Ulcer: A typical patient will have a chronic ulcer over his/her tibia. An ointment is formulated having the following composition: white petrolatum (70% v/v); emulsifying waxNF (5% v/v); propylene glycol (10% v/v); propylene carbonate (5% v/v); glyceryl monostearate (5% v/v); white wax (5% v/v); and an NO• inducer (0.4 mg/ml of ointment). The ointment is rubbed into the wound for 5 minutes twice a day until the wound has healed.

C. Soft Tissue Injury: For treatment of a hamstring strain or other traumatic soft tissue injury, the ointment described in Section B above is rubbed into the skin over the painful area for 5 minutes twice a day, until the injury is pain-free.

EXAMPLE 4

Clinical Treatments Using an NOS Inhibitor

Following are clinical situations in which NO• inhibitors may be administered to prevent unwanted wound healing (i.e. fibrosis), and additionally to prevent arthritis.

A. Anterior Cruciate Ligament (ACL) Injury: During surgical reconstruction of an injured ACL, the patient's knee is cleansed with disinfectant, draped, and standard arthroscopic portals are established i.e. supero-medial, supero-lateral, infero-medial and infero-lateral. Inflow is established through one of the portals. The fluid that irrigates the knee joint at this point and throughout the surgery consists of Ringer's, solution (NaCl 8.6 g/L; CaCl2 330 mg/L; KCl 300 mg/L; 309 mOsm/L) containing a competitive inhibitor of NOS (e.g. L-NAME) at a concentration of 0.1 mg/ml. 10 ml of the same solution containing a higher concentration of NOS inhibitor (e.g. 1 mg/ml) is injected into the joint following surgery.

B. Frozen shoulder: This syndrome is defined as a loss of range of motion with or without pain and with no attributable cause. 10 ml of Ringer's solution as above, containing 1 mg/ml of an NOS inhibitor, is injected into the joint.

EXAMPLE 5

Sustained Release Formulations

A sustained-release formulation of a NONOate for implantation in a wound is formulated as follows: 20 g DETA/NO and 80 g polylactic acid-polyglycoilic acid (PLAGA) are dissolved in 100 ml methyl chloride. 0.5 g polyvinyl alcohol is added. The mixture is stirred for 24 hours, until the solvent has evaporated. The resulting microspheres are washed in distilled water and freeze-dried, after which they are stored under nitrogen at −20° C.

A sustained-release formulation of an NOS inhibitor for prevention of excessive scar formation e.g. around surgical implants is formulated as follows: 20 g of an NOS inhibitor such as L-NAME and 80 g polylactic acid-polyglycolic acid (PLAGA) are dissolved in 100 ml methyl chloride. 0.5 g polyvinyl alcohol is added. The mixture is stirred for 24 hours, until the solvent has evaporated. The resulting microspheres are washed in distilled water and freeze-dried, after which they are stored under nitrogen at −20° C.

What is claimed is:

1. A method for promoting the healing of damaged tissue in a patient in need of such treatment, comprising exposing said tissue to an effective amount of an agent that increases local concentration of nitric oxide compared to the concentration of nitric oxide in said tissue in the absence of said agent, wherein said tissue is a member selected from the group consisting of muscle, tendon, ligament, and bone, said damage comprises surgical incisions, traumna, and endogenous pathological processes and said healing comprises the recruitment of inflammatory cells, followed by fibroblasts, to the site of the tissue damage.

2. The method of claim 1 which comprises administering said agent in a manner that places said agent in contact with said damaged tissue.

3. The method of claim 1 which comprises increasing the activity of nitric oxide synthase by administration of said agent.

4. The method of claim 1 which comprises administering a compound that releases NO as a breakdown product.

5. The method of claim 1 which comprises administering said agent up to 96 hours after the occurrence of said damage.

6. The method of claim 1 which comprises administering said agent via the intravenous, intramuscular, intraarticular, nasal, or topical route.

7. The method of claim 1 which comprises increasing said concentration of nitric oxide to between about 150% and about 10,000% of the nitric oxide concentration present in the absence of said agent.

* * * * *

UNITED STATES PATENT AND TRADEMARK OFFICE
CERTIFICATE OF CORRECTION

PATENT NO. : 6,190,704 B1  Page 1 of 1
APPLICATION NO. : 08/311545
DATED : February 20, 2001
INVENTOR(S) : George Anthony Calvert Murrell It is certified that error appears in the above-identified patent and that said Letters Patent is hereby corrected as shown below:

In Column 16, Line 2 (Claim 1), please delete "muscle,".

Signed and Sealed this

Twentieth Day of March, 2007

JON W. DUDAS
*Director of the United States Patent and Trademark Office*